United States Patent [19]  
Lodewyk

[11] 4,076,745  
[45] Feb. 28, 1978

[54] PROCESS FOR CALCIUM SALTS α-KETOCARBOXYLIC ACIDS

[75] Inventor: Eric Lodewyk, Boulder, Colo.

[73] Assignee: Syntex (U.S.A.) Inc., Palo Alto, Calif.

[21] Appl. No.: 703,498

[22] Filed: Jul. 8, 1976

[51] Int. Cl.$^2$ .................. C07C 53/24; C07C 87/08
[52] U.S. Cl. ........................ 260/526 R; 260/501.1
[58] Field of Search ........ 260/502 R, 586 D, 610 SK, 260/502 A, 515, 514 R, 561 A, 530 R, 525 R, 526 R, 501.1

[56] References Cited  
U.S. PATENT DOCUMENTS

B 426,157  3/1976  Lannert ........................ 260/535 P

FOREIGN PATENT DOCUMENTS 1,028,930  3/1965  United Kingdom .............. 260/501.1

Primary Examiner—James O. Thomas, Jr.  
Assistant Examiner—Werren B. Lone  
Attorney, Agent, or Firm—Alan M. Krubiner

[57] ABSTRACT

A process for the preparation of calcium salts of α-ketocarboxylic acids comprising reacting an α-ketocarboxylic acid with an amine, to afford a salt, said salt being soluble in the reaction medium, treating said salt with a source of calcium ion to afford the calcium salt of the α-ketocarboxylic acid, said salt being substantially insoluble in said reaction medium, and isolating said calcium salt from the reaction medium. This process is especially useful for the preparation of calcium salts of α-keto analogues of essential α-amino acids.

1 Claim, No Drawings

PROCESS FOR CALCIUM SALTS α-KETOCARBOXYLIC ACIDS

BACKGROUND OF THE INVENTION

α-Ketocarboxylic acids are a valuable class of chemical compounds having utility in chemical synthesis, biochemical processes, and the like. It has recently been discovered that α-keto analogues of essential α-amino acids, and salts thereof, are highly effective for the treatment of patients suffering from chronic kidney failure, i.e., uremic poisoning. See, for example, Walser, Clinical Nephrology, Vol. 3, pp. 178–186 (1975) and citations therein. Calcium salts of such α-ketocarboxylic acids are especially important, since the use of calcium rather than e.g., sodium, as the cation substantially reduces problems of ionic balance, which are particularly critical in the case of kidney disorders.

Accordingly, it would be highly desirable to have available a simple, high yield, economical process that can be readily adapted for large-scale production of calcium salts of such α-ketocarboxylic acids.

There are a number of methods for preparing calcium salts of carboxylic acids that are well known in the art and that could be initially considered in the instant situation. One method involves the preparation of a water soluble alkali metal salt followed by precipitation of the calcium salt by exchange, for example, by treatment with a solution of a calcium halide. However, such a method does not work in the instant case since the calcium salts of interest with the exception of calcium α-ketoisocaproate, are substantially water soluble. Another method involves the preparation of a calcium salt from the free acid by treatment with calcium carbonate in water, followed by concentration of the aqueous solution of the calcium salt thus formed. In the case of calcium α-ketoisovalerate and calcium α-keto-β-methylvalerate, such method, while operable, is tedious to perform on a large scale.

DETAILED DESCRIPTION OF THE INVENTION

The present invention relates to a process for the preparation of calcium salts of α-ketocarboxylic acids.

More specifically, the present invention is concerned with the preparation of calcium salts of α-ketocarboxylic acids which are analogues of essential α-amino acids, especially calcium salts of α-ketocarboxylic acids represented by Formula (I)

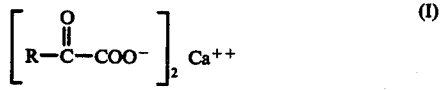

wherein R is lower alkyl. As used herein, the term "lower alkyl" comprehends straight or branched chain saturated hydrocarbon radicals having from one to eight carbon atoms, such as methyl, ethyl, n-propyl, isopropyl, n-butyl, sec-butyl, tert-butyl, n-hexyl, n-octyl, and the like.

The calcium salts of the following α-ketocarboxylic acids are of particular interest: α-ketoisovaleric acid (α-keto analogue of valine), α-ketoisocaproic acid (α-keto analogue of leucine), and α-keto-β-methylvaleric acid (α-keto analogue of isoleucine).

The instant invention may be more completely characterized as a process for the production of calcium salts of α-ketocarboxylic acids comprising:

(a) treating an α-ketocarboxylic acid with an amine in a solvent medium to afford a salt of said α-ketocarboxylic acid and said amine, said salt being soluble in said reaction medium, (b) treating the product of step (a) with a source of calcium ion to produce the calcium salt of said α-ketocarboxylic acid, said salt being substantially insoluble in said reaction medium, and (c) isolating said substantially insoluble calcium salt from the reaction medium.

Thus, the process of the present invention provides a simple means for preparing calcium salts, since the starting reactants, the intermediate keto acid-amine salt and the by-product inorganic amine salt are soluble in the reaction medium, and the final product, i.e., the desired calcium salt, is insoluble in the reaction medium and is readily separated therefrom and purified.

Particularly preferred reaction media for the carrying out of the present process comprise methanol, ethanol or mixtures thereof. Methanol is a particularly preferred reaction medium.

As amines which are particularly useful for the present process there may be mentioned tri(lower alkyl)amines, such as trimethylamine, triethylamine, tri(n-butyl)amine, and the like; aromatic amines such as, for example, pyridine, quinoline, isoquinoline, and the like; and cyclic amines such as, for example, N-methylpyrrolidine, N-methylpiperidine, and the like. Triethylamine is a particularly preferred amine for use in the present process.

While the proportions of the keto acid and amine reagents may be varied over a wide range, it is generally preferred to use an approximately equimolar amount of the organic amine relative to the α-keto acid, and preferably a slight excess, e.g. a ten mole percent excess, of the amine.

The reagents may be contacted in any manner commonly employed in the art. However, it is preferred to add the keto acid to a solution of the amine in the solvent medium.

The temperature for this portion of the reaction may vary over a wide range, for example, from about 0° to about 40° C; however, a preferred temperature range is from about 10° to 25° C.

In the next portion of the reaction sequence, the keto acid-amine salt formed in situ during the previous step is reacted with a source of calcium ion. Representative of calcium ion sources that may be mentioned for this purpose are calcium salts that are substantially soluble in the reaction medium, e.g., calcium chloride, calcium bromide, calcium nitrate, calcium acetate, and the like. Calcium chloride is particularly preferred.

The calcium salt may be added as a solid, or preferably, as a solution in the reaction medium being employed. The quantity of calcium salt utilized will normally be at least one-half mole per mole of keto-acid-amine salt, preferably a slight excess relative to the keto acid-amine salt.

The two reactants may be contacted in any manner commonly employed in the art for such reaction, although it is preferred to add the keto acid-amine salt to the calcium salt. This portion of the reaction sequence may be carried out at a temperature between about 0° and about 80° C, preferably between about 20° and 60° C. In a preferred embodiment, the reactants are contacted at a temperature of about 25° C and the reaction mixture maintained at a temperature between about 20° and 30° C to allow for the precipitation of the calcium salt of Formula (I). Depending upon the solubility characteristics of the final product calcium salt of Formula (I), adjustment of the temperature above or below this temperature range may be performed to optimize the yield of the final product, such variations being readily determinable by routine experimental procedures.

The precipitated calcium salt of Formula (I) may be isolated from the reaction medium by standard methods, for example, by filtration, centrifugation, decantation, and the like. The separated solid salt is preferably washed with a fresh portion of solvent medium to remove impurities and is then dried to remove excess solvent.

Calcium salts of α-ketocarboxylic acids produced in accordance with the above method are high quality solids requiring little if any further purification, and are obtained in yields generally between about 80 and 95 percent of theory.

The following examples illustrate specific embodiments of the process of the present invention. They are illustrative only and should not be considered limitative of the scope or spirit of the invention in any manner.

EXAMPLE 1

A solution of 11.1 grams (0.11 moles) of triethylamine in 100 ml. of methanol was treated slowly with 16.6 grams (0.1 mole) of α-ketoisovaleric acid while keeping the temperature at or below 25° C. This mixture was then added, over 30 minutes, to a filtered solution of 5.5 grams (0.1 mole) calcium chloride in 100 ml. of methanol keeping the reaction mixture at 25° C. After completion of addition, the slurry was stirred for an additional 30 minutes and the calcium salt isolated by filtration, washed with 50 ml. of methanol and dried at 40° C for 24 hours. Yield = 12.1 grams (90%) of a brilliant white fluffy powder having 100.1% (dry basis) of theoretical Ca.

EXAMPLE 2

Similarly, proceeding as in Example 1, and replacing α-ketoisovaleric acid with α-ketoisocaproic acid and α-keto-β-methylvaleric acid, there are prepared the corresponding calcium salts of these acids, respectively.

Calcium α-ketoisocaproate, yield = 93%; Assay (Ca) on a dry basis = 99.9%.

Calcium α-keto-β-methylvalerate, yield = 87%; Assay (Ca) on a dry basis = 99.7%.

What is claimed is:

1. A process for the preparation of a calcium salt of an α-ketocarboxylic acid selected from the group consisting of α-ketoisovaleric acid, α-ketoisocaproic acid, and α-keto-β-methylvaleric acid, which process comprises:
   (a) treating said α-ketocarboxylic acid with substantially an equimolar amount of triethylamine in methanol at a temperature between about 0° and 40° C for a sufficient period of time to afford a methanolic solution of the triethylamine salt of said α-ketocarboxylic acid,
   (b) treating the product of step (a) with a methanolic solution of substantially one-half mole calcium chloride relative to said triethylamine salt at a temperature between about 0° and 80° C for a sufficient period of time to afford a precipitate of the calcium salt of said α-ketocarboxylic acid, and
   (c) isolating said calcium salt.

* * * * *